United States Patent
Walton (10) Patent No.: US 9,052,294 B2
(45) Date of Patent: Jun. 9, 2015

(54) METHOD AND SYSTEM FOR TWO-DIMENSIONAL AND THREE-DIMENSIONAL INSPECTION OF A WORKPIECE

(75) Inventor: Steven R. Walton, Buckley, WA (US)

(73) Assignee: The Boeing Company, Chicago, IL (US)

( * ) Notice: Subject to any disclaimer, the term of this patent is extended or adjusted under 35 U.S.C. 154(b) by 2230 days.

(21) Appl. No.: 11/421,273

(22) Filed: May 31, 2006

(65) Prior Publication Data
US 2007/0280501 A1 Dec. 6, 2007

(51) Int. Cl.
*G06K 9/00* (2006.01)
*G01N 21/88* (2006.01)
*G06T 7/00* (2006.01)
*G01N 21/84* (2006.01)

(52) U.S. Cl.
CPC .... *G01N 21/8806* (2013.01); *G01N 2021/8472* (2013.01); *G01N 2201/0626* (2013.01); *G01N 2201/0627* (2013.01); *G06T 7/0004* (2013.01); *G06T 2207/10152* (2013.01); *G06T 2207/30164* (2013.01)

(58) Field of Classification Search
USPC .......................................................... 382/100
See application file for complete search history.

(56) References Cited

U.S. PATENT DOCUMENTS

| | | |
|---|---|---|
| 4,098,130 A | 7/1978 | Coffey et al. |
| 4,417,149 A | 11/1983 | Takeuchi et al. |
| 4,545,251 A | 10/1985 | Uchida et al. |
| 4,672,678 A | 6/1987 | Koezuka et al. |
| 4,699,683 A | 10/1987 | McCowin |
| 4,706,296 A | 11/1987 | Pedotti et al. |
| 4,790,023 A | 12/1988 | Matsui et al. |
| 4,875,372 A | 10/1989 | Gilbert |
| 4,975,863 A | 12/1990 | Sistler et al. |
| 5,012,523 A | 4/1991 | Kobayashi et al. |
| 5,032,211 A | 7/1991 | Shinno et al. |

(Continued)

FOREIGN PATENT DOCUMENTS

| | | |
|---|---|---|
| EP | 0 833 146 A2 | 4/1998 |
| EP | 1 072 884 A2 | 1/2001 |

(Continued)

OTHER PUBLICATIONS

Malamas et al A survey on industrial vision systems, applications and tools Image and vision Computing 21 (2003) pp. 171-188.*

(Continued)

*Primary Examiner* — Mark Roz
(74) *Attorney, Agent, or Firm* — Alston & Bird LLP (57) ABSTRACT

A system and method for inspecting a workpiece are provided. According to one embodiment, the system includes a plurality of illumination sources positioned proximate to the workpiece and each operable to generate at least one respective illumination beam to illuminate at least a portion of the workpiece, wherein each beam has a different respective color. The system also includes at least one camera positioned proximate to the workpiece and operable to capture at least one image of at least a portion of the workpiece including the illumination beams incident thereon. In addition, the system includes a data system capable of providing simultaneous two-dimensional and three-dimensional information indicative of the workpiece based on the image acquired by the camera.

11 Claims, 4 Drawing Sheets

(56) References Cited

U.S. PATENT DOCUMENTS

| | | |
|---|---|---|
| 5,189,481 A | 2/1993 | Jann et al. |
| 5,231,675 A | 7/1993 | Sarr et al. |
| 5,341,183 A | 8/1994 | Dorsey-Palmateer |
| 5,349,860 A | 9/1994 | Nakano et al. |
| 5,388,318 A | 2/1995 | Petta |
| 5,444,505 A | 8/1995 | Dorsey-Palmateer |
| 5,450,147 A | 9/1995 | Dorsey-Palmateer |
| 5,506,641 A | 4/1996 | Dorsey-Palmateer |
| 5,562,788 A | 10/1996 | Kitson et al. |
| 5,651,600 A | 7/1997 | Dorsey-Palmateer |
| 5,663,795 A | 9/1997 | Rueb |
| 5,671,053 A | 9/1997 | Wigg et al. |
| 5,703,784 A | 12/1997 | Pearson |
| 5,742,504 A | 4/1998 | Meyer et al. |
| 5,745,176 A | 4/1998 | Lebens |
| 5,815,275 A | 9/1998 | Svetkoff et al. |
| 5,862,372 A | 1/1999 | Morris et al. |
| 6,017,125 A | 1/2000 | Vann |
| 6,064,429 A | 5/2000 | Belk et al. |
| 6,070,466 A | 6/2000 | Taran et al. |
| 6,120,446 A | 9/2000 | Ji et al. |
| 6,122,065 A | 9/2000 | Gauthier |
| 6,381,366 B1 | 4/2002 | Taycher et al. |
| 6,408,429 B1 | 6/2002 | Marrion, Jr. et al. |
| 6,480,271 B1 | 11/2002 | Cloud et al. |
| 6,639,660 B1 | 10/2003 | Beck et al. |
| 6,694,164 B2 | 2/2004 | Glossop |
| 6,723,951 B1 | 4/2004 | McGraw |
| 6,744,913 B1 | 6/2004 | Guest et al. |
| 6,799,619 B2 | 10/2004 | Holmes et al. |
| 6,871,684 B2 * | 3/2005 | Engelbart et al. ............. 156/361 |
| 7,193,696 B2 | 3/2007 | Engelbart et al. |
| 7,590,442 B2 | 9/2009 | Boese et al. |
| 7,678,214 B2 | 3/2010 | Engelbart et al. |
| 2002/0141632 A1 | 10/2002 | Engelbart et al. |
| 2003/0102070 A1 | 6/2003 | Black et al. |
| 2004/0060650 A1 | 4/2004 | Holmes et al. |
| 2004/0189944 A1 | 9/2004 | Kaufman et al. |
| 2004/0257540 A1 | 12/2004 | Roy et al. |
| 2005/0058332 A1 | 3/2005 | Kaufman et al. |
| 2005/0082262 A1 | 4/2005 | Rueb et al. |
| 2005/0116952 A1 | 6/2005 | Je et al. |
| 2005/0121422 A1 | 6/2005 | Morden et al. |
| 2006/0073309 A1 | 4/2006 | Hogg |
| 2006/0108048 A1 | 5/2006 | Engelbart et al. |
| 2007/0034313 A1 | 2/2007 | Engelbart et al. |
| 2007/0097359 A1 | 5/2007 | Engelbart et al. |
| 2007/0172129 A1 | 7/2007 | Tortora et al. |
| 2007/0271064 A1 | 11/2007 | Walton |
| 2007/0280501 A1 | 12/2007 | Walton |
| 2008/0055591 A1 | 3/2008 | Walton |

FOREIGN PATENT DOCUMENTS

| | | |
|---|---|---|
| EP | 1 334 819 A1 | 8/2003 |
| EP | 1 503 206 A1 | 2/2005 |
| EP | 1 574 845 A1 | 9/2005 |
| FR | 2188836 | 1/1974 |
| GB | 1 590 571 A | 6/1981 |
| GB | 2 143 423 A | 2/1985 |
| JP | 59-60327 | 4/1984 |
| JP | 59060327 * | 4/1984 |
| JP | 06-273349 A | 9/1994 |
| JP | 8-247736 | 9/1996 |
| JP | 10-221308 | 8/1998 |
| JP | 2002-323454 | 11/2002 |
| WO | WO 99/00661 A1 | 1/1999 |
| WO | WO 00/70303 | 11/2000 |
| WO | WO 02/12870 A2 | 2/2002 |
| WO | WO 02/29357 A2 | 4/2002 |
| WO | WO 02/073173 A2 | 9/2002 |

OTHER PUBLICATIONS

J H Kim and H S Cho Neural network-based inspection of solder joints using a circular illumination Image and Vision Computing vol. 13 No. 6 Aug. 1995.*

David W. Capson and Sai-Kit Eng A Tiered-Color Illumination Approach for Machine Inspection of Solder Joints IEEE Transactions on Pattern Analysis and Machine Intelligence, vol. IO. No. 3. May 1988.*

International Search Report and Written Opinion for International Appl. No. PCT/US2007/012858, mailed Jan. 22, 2008.

Paulson, et al., "Infrared Imaging Techniques for Flaw Detection in Composite Materials," Proceedings of the SPIE, Bellingham, Virginia, vol. 366, Aug. 26, 1982, pp. 88-95.

Asla M. Sa, Paulo Cezar Carvalho, and Luiz Velho; *Recovering Registered Geometry and High Dynamic Range Texture with Coded Structure Light*; pp. 1-4. Printed from website http://www.wscg.zcu.cz/wscg2003/Papers_2003/E03.pdf. (2003).

Li Zhang, Brian Curless, and Steven M. Seitz, Department of Computer Science and Engineering, University of Washington;*Rapid Shape Acquisition Using Color Structured Light and Multi-pass Dynamic Programming*; pp. 1-13; 13 pages printed from website http://www.grail.cs.washington.edu/projects/moscan/paper.pdf on Mar. 27, 2006.

Asla M. Sa, Paulo Cezar Carvalho, and Luiz Velho;-*BCSL: Structured Light Color Boundary Coding for 3D Photography*; VMV 2002; pp. 1-9; Erlangen, Germany, Nov. 20-22, 2002. Printed from website http://vvww.visgraf.impa.br/Data/RefBib/PS_PDF/vmv02/bs-BCSL.pdf.

*3D Images Using Color Structured Light*; Way-2C Color Machine Vision—3D Images Using Color Structured Light; 2 pages printed from website http://www.way2c.com/w2csl.htm on Mar. 27, 2006.

U.S. Appl. No. 11/202,411, Engelbart et al.

U.S. Appl. No. 11/383,681, Savol et al.

U.S. Appl. No. 11/470,403, Walton.

Bennett et al.; "Experimental Optical Fan Beam Tomography"; *Applied Optics;* vol. 23, No. 16; Aug. 15, 1984; pp. 2678-2685.

Jagannathan S., et al.; "Intelligent Inspection of Wave-Soldered Joints"; *Journal of Manufacturing Systems;* 1992; vol. 11, No. 2; pp. 137-143.

Jiminez, A.R. et al.; "Automatic Fruit Recognition: A Survey and New Results Using Range/Attenuation Images"; *Pattern Recognition*, 32(10), pp. 1719-1736, 1999.

Sharp R et al.; "Material Selection/Fabrication Issues for Thermoplastic Fiber Placement"; *Journal of Thermoplastic Composite Materials;* vol. 8; Jan. 1995; pp. 2-13.

Communication from European Patent Application No. 07777339.8, dated Jan. 16, 2012.

Communication from European Patent Application No. 07777339.8, dated Jun. 22, 2010.

Extended European Search Report from European Patent Application No. 08251727.7, dated Sep. 10, 2008.

Extended European Search Report from European Patent Application No. 07251939.0, dated Aug. 7, 2007.

Communication from European Patent Application No. 07251939.0, dated Feb. 13, 2012.

International Search Report from International Application No. PCT/US2006/045851, dated Apr. 23, 2007.

Written Opinion from International Application No. PCT/US2006/045851, dated Apr. 23, 2007.

International Preliminary Report on Patentability from International Application No. PCT/US2006/045851, dated Jun. 3, 2008.

U.S. Appl. No. 11/383,681, Final Office Action dated Apr. 14, 2011, (20 pgs).

U.S. Appl. No. 11/383,681, Non-Final Office Action dated Sep. 20, 2010, (15 pgs).

U.S. Appl. No. 11/383,681, Final Office Action dated Jun. 9, 2010, (12 pgs).

U.S. Appl. No. 11/383,681, Non-Final Office Action dated Jan. 28, 2010, (8 pgs).

EP Communication Pursuant to Rule 62 EPC, Application No. EP 08251727, Sep. 10, 2008, European Patent Office (5 pages).

(56) References Cited

OTHER PUBLICATIONS

U.S. Appl. No. 11/805,156, Non-Final Office Action dated Mar. 4, 2011.
U.S. Appl. No. 11/805,156, Notice of Allowance dated Jul. 8, 2011.
International Search Report and Written Opinion from International Patent Application No. PCT/US2006/034114 dated Nov. 30, 2006.
U.S. Appl. No. 11/293,443, Non-Final Office Action dated May 9, 2007.
U.S. Appl. No. 11/293,443, Non-Final Office Action dated Oct. 25, 2007.
U.S. Appl. No. 11/293,443, Non-Final Office Action dated Mar. 27, 2008.
U.S. Appl. No. 11/293,443, Notice of Allowance dated Oct. 7, 2008.
Assembly Guidance Systems—Automatic Ply Verification [online] [retrieved Sep. 30, 2014]. Retrieved from the Internet: <URL:http://web.archive.org/web/20051003221116/http://www.assemblyguide.com/HAMPI/Hampi.htm>. (dated Sep. 30, 2014) 3 pages.
UltraOptec Luis 747 [online] [retrieved Sep. 30, 2014]. Retrieved from the Internet: URL:http://www.web.archive.org/web/20030612021058/ultraoptec.com/luis-747/LUIS-747.html>. (dated Sep. 30, 2014) 14 pages.

* cited by examiner

METHOD AND SYSTEM FOR TWO-DIMENSIONAL AND THREE-DIMENSIONAL INSPECTION OF A WORKPIECE

BACKGROUND OF THE INVENTION

1) Field of the Invention

Embodiments of the present invention relates to the inspection of a workpiece and, more particularly, to systems and methods for providing two-dimensional and three-dimensional information indicative of a workpiece.

2) Description of Related Art

Composite structures are commonly manufactured by progressively building up the structure with a plurality of layers of thin composite tape (or tow) laid one layer upon another. Typically, the operation begins by laying one or more tapes onto a starting template or tool that has a configuration generally corresponding to the desired shape of the article to be produced. A tape placement head of a manufacturing system moves over the surface of the template, guiding the one or more tapes of composite material onto the template. The head usually makes repeated passes over the template in a defined pattern until the composite material is entirely collated, building up successive layers of the composite tape to form the desired workpiece. A compaction roller is typically used for pressing the tape against the workpiece, thereby facilitating adhesion of the successive layers. The workpiece may then be subjected to a curing process (e.g. heating) to further adhere and bond the composite layers. Conventional systems for forming composite structures using successive layers of tape include those systems disclosed, for example, in U.S. Pat. No. 6,799,619 issued to Holmes et al., and U.S. Pat. No. 6,871,684 issued to Engelbart et al.

The measurement accuracy required by the manufacturing specification, which is in turn driven by design requirements, in areas such as ply boundaries, tape edge gaps and overlaps, material wrinkles, and the presence of foreign object debris (FOD), has created a need to make those measurements with a robust automated system. Prior and emerging art, using various machine vision technologies, have provided limited capabilities to meet these requirements. As such, manual visual inspection of composite plies is frequently employed, which may be unreliable, inefficient, and subject to operator error. Namely, the machine must be stopped and the process of laying materials halted until the inspection is complete. During the inspection, the operator verifies the dimensions of any suspect defects and quantifies the number of defects per given unit area. The defects are repaired as needed and laying of the next ply proceeds. Therefore, current visual inspection techniques are insufficient to move into a production environment with systems that require efficient and reliable inspection of the workpiece.

It would therefore be advantageous to provide systems and methods for inspecting a workpiece to increase the reliability and accuracy of the inspection of the workpiece. In addition, it would be advantageous to provide systems and methods to increase the quality of a workpiece, the production rate, and inspection efficiency, as well as reduce the overall cost of the manufacturing and inspection processes.

BRIEF SUMMARY OF THE INVENTION

Embodiments of the invention may address at least some of the above needs and achieve other advantages by providing systems and methods for inspecting a workpiece. Generally, embodiments of the present invention utilize laser generators and/or light-emitting diode (LED) arrays of various geometric configurations to illuminate a workpiece with fan beams and/or specifically-shaped light washes having different respective colors. A camera captures an image indicative of the portion of the workpiece illuminated by the laser generators and/or LED arrays such that a data system can process the image to generate information indicative of the workpiece. The laser generators and/or LED arrays are configured to illuminate the workpiece such that embodiments of the present invention are capable of providing both two-dimensional and three-dimensional information indicative of the workpiece, as well as capable of providing such information during processing of the workpiece.

In one embodiment of the present invention, a system for inspecting a workpiece is provided. The system includes a plurality of illumination sources (e.g., one laser generator and two LED arrays) positioned proximate to the workpiece and each operable to illuminate at least a portion of the workpiece with at least one respective illumination beam (e.g., a fan beam or structured LED light wash), wherein each illumination source has a different respective color. The system also includes at least one camera positioned proximate to the workpiece that is operable to capture one or more images of at least a portion of the workpiece in response to illumination of at least a portion of the workpiece by the illumination beam. In addition, the system includes a data system capable of providing two-dimensional and three-dimensional information indicative of the workpiece based on the image acquired by the camera.

According to various modifications of the system of the present invention, the illumination sources produce respective illumination beams that are configured to illuminate a respective feature of the workpiece, such as respective edges of a gap in the workpiece. In addition, each of the laser generators and/or LED arrays may be positioned to provide a respective fan beam and/or light wash that illuminates the workpiece at an oblique incidence angle. Furthermore, the data system may provide information indicative of respective edges of a workpiece, a gap in the workpiece, a topology of the workpiece, a shape of the workpiece, and/or a flaw in the workpiece. The data system may also combine information attributable to the illumination beams that are generated by each of the plurality of illumination sources and that are independent from one another, and/or provide information indicative of the workpiece during processing of the workpiece.

An additional aspect of the present invention provides a method for inspecting a workpiece. The method includes illuminating at least a portion of the workpiece with a plurality of colored illumination beams (e.g., fan beams and light washes), and capturing at least one image of at least a portion of the workpiece illuminated by the illumination beams. In addition, the method includes providing two-dimensional and three-dimensional information indicative of the workpiece based on the captured image.

According to variations of the method, the method further includes performing a manufacturing process on a moving workpiece during the illuminating and capturing steps, while the illuminating step may include illuminating at least a portion of the workpiece with at least one colored illumination beam in a direction substantially perpendicular to the moving workpiece. The method could also include combining information that is attributable to each of the plurality of illumination beams and that is independent from one another. The providing step may include providing information indicative of respective edges of a workpiece, a gap in the workpiece, a topology of the workpiece, a shape of the workpiece, and/or a flaw in the workpiece. The illuminating step could include illuminating the plurality of colored illumination beams with respective illumination sources (e.g., laser generator or LED array). Moreover, the providing step could alternatively include determining the color of a respective colored illumination beam, a shape of a respective colored illumination beam, a location of a respective illumination source, and/or a pointing direction of a respective illumination source. The illuminating step may include illuminating the workpiece with a respective colored illumination beam at an oblique incidence angle.

A further aspect of the present invention includes an inspection system for inspecting a composite workpiece laminated with composite tape plies. The system includes a plurality of illumination sources (e.g., laser generators and/or LED arrays) positioned proximate to the workpiece and each operable to illuminate at least a portion of the workpiece with at least one respective illumination beam (e.g., fan beam or light wash), as well as a camera positioned proximate to the workpiece and operable to capture at least one image of at least a portion of the workpiece in response to illumination of at least a portion of the workpiece by the illumination beams. Each of the illumination beams may be a respective color. The system further includes a data system capable of providing information (e.g., two-dimensional and three-dimensional information) indicative of the workpiece based on the image acquired by the camera. The system may provide information indicative of respective edges of a tape ply, a gap between tape plies, a topology of a tape ply, a wrinkle in a tape ply, and/or a flaws in a tape ply.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
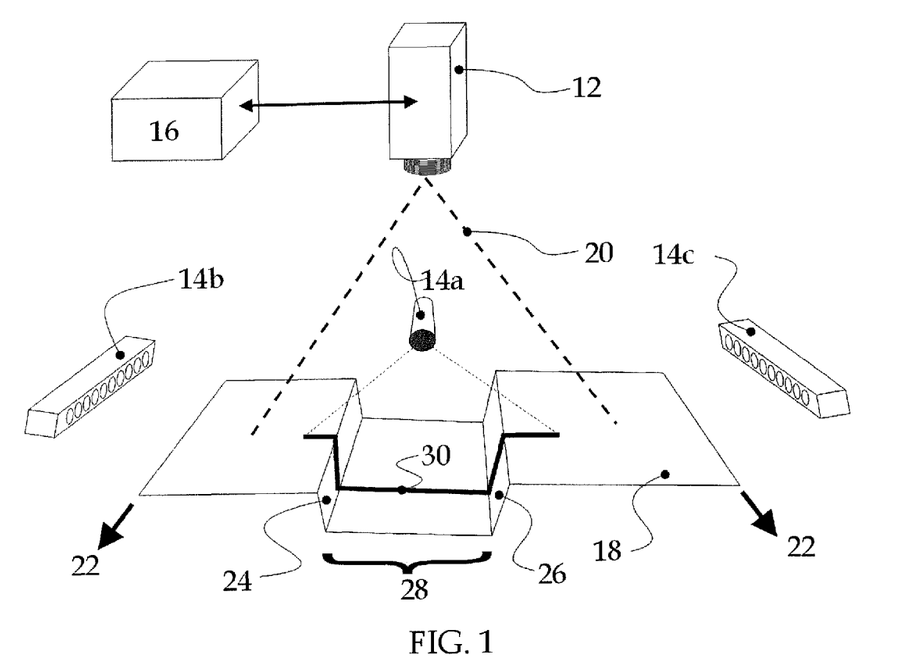
FIG. 1 is a perspective view of an inspection system according to one embodiment of the present invention.

Referring now to the drawings and, in particular to FIG. 1, there is shown an inspection system for identifying and locating features in a workpiece. The system 10 includes a camera 12 and a plurality of illumination sources 14*abc*, in some combination determined by the type of workpiece to be inspected, that cooperate to acquire data indicative of the workpiece 18. The camera 12 and illumination sources 14*abc* are in communication with a data system 16 such that the data system may provide and/or process data captured by the camera. For example, the data system 16 could provide characteristic information of a feature captured by the camera 12. As will be explained in further detail below, the inspection system 10 utilizes both two-dimensional (2D) and three-dimensional (3D) information in conjunction with in-process inspection such that more efficient and reliable detection and characterization of features in the workpiece 18 are provided.

The term "feature," as used herein, is not meant to be limiting, as a feature could be any aspect, discontinuity, imperfection, defect, or flaw in the workpiece that may require attention by a technician, such as for repair or replacement of the workpiece or a portion of the workpiece. For example, a flaw could be a material wrinkle or foreign object debris ("FOD"), such as paper, plastic sheet, resin balls, carbon fiber "fuzzballs," or other material inimical to the production of composite parts. Moreover, the system 10 can detect the presence of features associated with the workpiece that would not ordinarily be characterized as a "flaw," such as a ply boundary, topology, shape/contour, or a tape edge gap or overlap, the positioning of which are requirements of the engineered workpiece design specification.

The inspection system 10 could be used to inspect any number of workpieces in a variety of industries where detection of features of the workpiece is required or desired, such as in the aircraft, automotive, or construction industries. Thus, the term "workpiece" is also not meant to be limiting, as the inspection system 10 could be used to inspect any number of parts or structures of different shapes and sizes, such as machined forgings, castings, or panels. For instance, the inspection could be performed on newly manufactured workpieces or existing workpieces that are being inspected for preventative maintenance purposes. Further, the workpiece could be any number of composite, plastic, and/or metallic materials.

Moreover, the system 10 could be used during the assembly or processing of the workpiece (e.g., as composite tape is being laid upon a mandrel), as well as before or after assembly for providing information characteristic of the workpiece. For example, the system 10 could be utilized during the manufacture of aircraft wing skins or stringers, such as in conjunction with a lamination machine for laying onto a workpiece composite tape (typically 1" or wider material) or tow (typically less than 1" in width) plies of varying shapes. Differing width material may be applied to a given ply, depending upon engineering requirements. A lamination machine, as known to those skilled in the art, is a device for laying this resin-impregnated carbon fiber material onto a mandrel to form a workpiece and can have various configurations. For instance, the lamination machine could include a gantry and a plurality of tape heads for laying down tape of composite material. The gantry is capable of translating so that tape is laid as the mandrel rotates and as the gantry translates longitudinally. However, although the system 10 is discussed herein in conjunction with a lamination machine for laying composite tape or tow plies onto a workpiece, the system could be employed to inspect various workpieces during various processes. The system 10 can be mounted onto a moving lamination head, a separate moving gantry, or statically on any portion of the machine that has appropriate access to the workpiece, and may be enabled, disabled, or dynamically reconfigured according to the requirements of a particular manufacturing process.

The inspection system 10 could also be used in conjunction with an image-projecting device. The image-projecting device could be any device capable of projecting a visible image onto the workpiece. For instance, the image-projecting device could be a laser projector or a digital projector capable of projecting an image indicative of a feature captured by the camera 12 such that the location of the feature can be readily identified. In addition, the image-projecting device could project images for facilitating the manufacture of the workpiece, such as a template for locating laminate plies during lay up of the composite tape. An exemplary projection system is disclosed in U.S. patent application Ser. No. 11/293,443, entitled "System for Projecting Flaws and Inspection Locations and Associated Method," which is assigned to the present assignee and incorporated herein by reference.

As described above, the camera 12 and illumination sources 14*abc* are employed to inspect a workpiece and communicate with a data system 16. In many cases, communications cable(s) of wire or optical fiber transmit data between the camera 12 and the data system 16. In other embodiments, the data may be transmitted between the camera 12 and the data system 16 via wireless communications. The camera 12 may be directly connected to the data system 16, or indirectly connected, such as via a network. In further embodiments of the present invention the data system 16 may be located proximate to the camera 12, such that remote connections between the camera and data acquisition system are not necessary.

The data system 16 could include a processor or similar computing device operating under the control of imaging software so that any features in the workpiece may be characterized. Although the data system 16 may process the data upon receipt, the data system may also include a memory device for storing the data, such as for subsequent review and analysis. Thus, the data system 16 could simply be a database for storing location information and/or data indicative of a feature, such that the information may accessed at a later time and processed by the same data system or another data system for characterizing features in the workpiece. The data system 16 is capable of generating data and/or images indicative of a feature of the workpiece and may also allow a user to store and edit previously generated data and/or images, such as in the memory device. However, it is understood that the data system 16 need not generate images, as the data system could mathematically collect and analyze data and generate, for example, location information of various workpiece features in terms of coordinates or the like.

In particular embodiments, the data system 16 is configured to display images representing data captured by the camera 12 in real time such that a real-time video display of the captured data may be shown. Also, in particular embodiments, the data system 16 is configured to allow a user to capture one or more still images of the data and, for example, to display the still images on a display screen or print the images. However, it should also be understood that the camera 12 may be adapted to capture images at pre-determined times and then to send the images to the data system 16 for display by a graphical interface or for output by an output device, such as a printer.

It is further understood that each camera 12 may include an associated data system 16, while each data system may, in turn, be in communication with a central data system. Thus, a central data system in such a tiered architecture could collect and/or further analyze images captured by respective cameras 12 and/or images or other data provided by respective data systems 16. In addition, the data system 16 includes a processor or other computing device that may be adapted to execute one or more applications (e.g., programs) and to otherwise operate under control of a standard operating system. For instance, the data system 16 may employ various software programs for processing and displaying the images captured by the camera 12. As will be explained in further detail below, the data system 16 and, more particularly, the software programs executed by the data system can employ various algorithms for analyzing and interpreting the images captured by the camera 12. Typically, the operating system and the various applications, e.g., software programs, are stored in the memory device or are otherwise accessible to the processor or other computing device.

The camera 12 is any suitable camera or other image capturing device capable of capturing data indicative of the workpiece such that the data system 16 can process the data and determine whether a flaw is present and/or provide information indicative of various features of the workpiece 18. In particular, the camera 12 typically captures images of the workpiece, and the data system 16 processes the images. The camera 12 is positioned to capture images generally perpendicular to the workpiece 18, although the camera could be located at other positions and/or orientations if desired, such as in instances in which the surface of the workpiece is non-planar or where a particular feature desired to be detected requires or is best imaged with a particular orientation of the camera. The inspection system 10 may include one or more cameras 12, such as a respective camera for each tape laying head. The camera 12 may be a commercially-available camera capable of acquiring color images, not necessarily limited to the visible spectrum of light. For example, in one embodiment, the camera 12 is a television or other type of video camera, an infrared-sensitive camera, a visible light camera with infrared-pass filtration, a fiber optic camera, a coaxial camera, Charge Coupled Device (CCD), or Complementary Metal Oxide Sensor (CMOS). The camera 12 may also include filter systems or other features by which one or more specific frequencies of light are recorded. The camera 12 can be positioned proximate the workpiece on a stand or mounted to a frame or similar device. For instance, the camera 12 could be carried proximate to a tape laying head on a lamination machine and translate along with a gantry.

The illumination sources 14*abc* typically include laser generators and/or LED arrays such that the illumination source is any device capable of illuminating the workpiece 18 with an illumination beam, such as a planar fan beam or shaped light wash. As shown in FIG. 1, there is a laser generator 14*a* and a pair of LED arrays 14*bc* that are capable of illuminating a workpiece 18 with a fan beam and light washes, respectively. A planar fan beam may be oriented by rotating around its optical axis such that the fan produces a line on the workpiece perpendicular to the optical axis of the laser generator, in the plane perpendicular to the workpiece described by the incidence angle of the laser generator, or at any angle in between. The pitch or roll angle of the illumination sources 14*abc* could also be varied to change the incidence angle of a respective illumination beam on the workpiece 18. Thus, the laser generator 14*a* could be a laser projector, a laser scanner, or the like capable of illuminating the workpiece 18 with a fan beam. The fan beam is generally a beam of light that spans outwardly in a plane from its origin location. Each LED array 14*bc*, as known to those of ordinary skill in the art, is generally an arrangement of bulbs for generating a light wash, such as a beam of light or other structured light that is configured to illuminate a specific feature on the workpiece 18. Each illumination source 14*abc* is capable of illuminating the workpiece 18 with structured light having a respective color (e.g., red, blue, and green) or additional specific spectral content.

Figure 3:
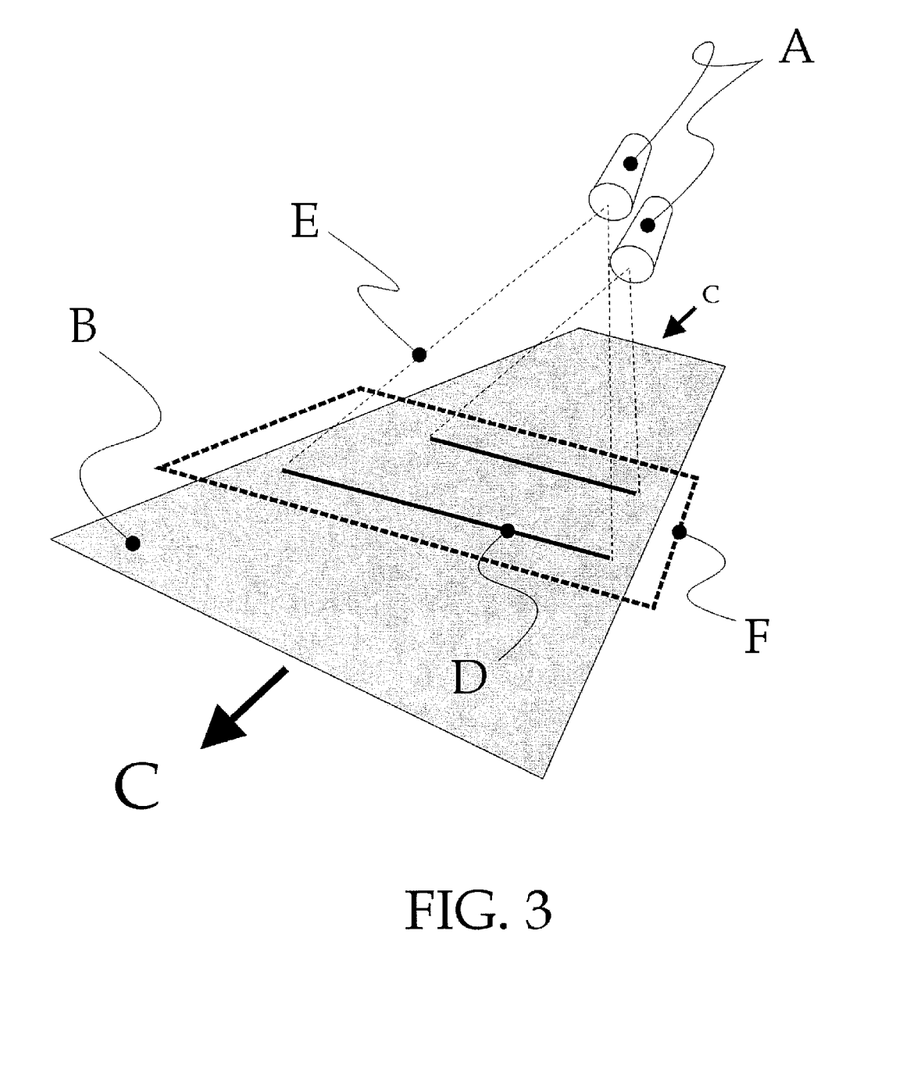
FIG. 3 is a perspective view of one method of applying more than one laser fan-beam illuminator to a given image frame.

The ability of the system 10 to resolve vertical changes in topology (e.g., a gap between adjacent tape courses that exposes the underlying ply layer) is inversely proportional to the total working depth of field (e.g., required if the workpiece moves significantly in the vertical direction with respect to the camera as the workpiece is inspected). The sensitivity of this relationship is determined by the incidence angle of the fan beam with respect to the surface. In the case of laser generators 14a, a plurality may be employed in a manner that a stack of parallel fan beams separated by some distance can increase the depth of field for in-process inspection, increase the surface sampling density so that small features are not missed during inspection, and enable the ability to utilize the same laser generators for large, static inspections by distributing a plurality of laser fan beam stripes over the surface of the entire workpiece. For example, FIG. 1 illustrates a laser generator 14a that is positioned to illuminate the workpiece 18 with a respective fan beam rotated such that the laser line drawn on the workpiece is perpendicular to the laser generator's optical axis, in the plane of the fan beam and within the camera's 12 field of view 20. Laser generator 14a might instead be a number of identical generators stacked on top of each other, or, alternatively, include an optical device that repeatedly replicates the fan beam such that each fan beam intersects the workpiece at slightly different incidence angles. One embodiment of this approach is illustrated in FIG. 3 wherein the workpiece B moves in direction C while being illuminated by two fan beam laser generators A, radiating fan beams E, to produce two samples of three dimensional information D. Note that in this arrangement the camera field of view F contains two three-dimensional samples across the workpiece instead of only one, thus doubling the effective sampling rate for any given camera frame rate.

Each of the illumination sources 14abc is configured in a specific geometric location and pointing direction depending on the type of feature desired to be detected. Additionally, an LED array 14bc may be of a specific shape to enhance particular features present in the workpiece. As shown in the embodiment illustrated by FIG. 1, the laser generator 14a is positioned to illuminate the workpiece 18 at an oblique incidence angle, where the incidence angle is an angle measured between a line drawn parallel to the workpiece and the fan beam. According to one aspect of the present invention, the incidence angle is shallow (e.g., less than about 30°). A range of incidence angles from approximately 5° to 30° may be employed in order to match the required measurement accuracy of tape laps and gaps to the desired vertical depth of field of the embodiment, and to generate more data indicative of surface debris in order to separate actual tape edges from common ridge-like structures in central regions of the workpiece 18. The edges 24, 26 of the workpiece 18 are generally parallel with the direction of movement of the workpiece (shown as direction of arrow 22) during processing. A pair of LED arrays 14bc are positioned to generate linear light washes that are generally parallel to the direction of movement of the workpiece 18 and more importantly parallel to the edges of gaps, while the laser generator 14a is positioned to generate a fan beam generally perpendicular to the direction of movement of the workpiece. The pair of LED arrays 14bc is thus configured to illuminate respective edges 24, 26 of a gap 28, while the laser generator 14a is capable of generating a fan beam configured as a line 30 on the workpiece 18 and thus highlighting a gap by the mechanism of a "step" in the laser line as seen by the camera 12. Each of the pair of LED arrays 14bc illuminates a respective edge 24, 26 on an opposite side of the gap 28, perpendicular to the laser generator 14a. Therefore, the opposing edges 24, 26 of the gap 28 may be differentiated when the pair of LED arrays 14bc and the laser generator 14a utilize colors that can be differentiated from one another.

It is understood that the number and configuration of the camera 12 and illumination generators 14abc shown in FIG. 1 are not meant to be limiting. In this regard, there may be any number of laser generators and/or LED arrays 14abc arranged in particular geometric configurations depending on the type of workpiece 18 being inspected and/or the features desired to be detected. In addition, there may be one or more cameras 12 utilized depending on the area of the workpiece 18 to be protected, as well as various other factors, such as the desired speed or accuracy of inspection. Furthermore, and as indicated above, the workpiece 18 may be various sizes and configurations and include features associated with the workpiece that are not limited to the particular gap 28 shown in FIG. 1. For example, the system 10 is capable of providing substantive and robust information indicative of respective edges of a workpiece, a topology of the workpiece, a shape of the workpiece, and a flaw in the workpiece (e.g., presence or location of the flaw). With respect to composite workpieces 18, the system 10 is further capable of providing information indicative of respective edges of a tape ply, a gap between tape plies, a topology of a tape ply, a wrinkle in a tape ply, and/or a flaw in a tape ply (e.g., FOD including paper, plastic sheet, resin balls, carbon fiber, "fuzzballs," or other material inimical to the production of composite workpieces.

At the lowest level in the system 10, each of the plurality of illumination sources 14abc may provide a specific and separate degree of information regarding location and type of a workpiece feature or portion of a feature, which may be a tape or tow gap or overlap, a topological or boundary measurement, an end-of-tape condition, presence or absence of specific tows within a course, twists or displacements of tows, puckered, torn or wrinkled tape, or a flaw comprised of various types of foreign object debris such as backing paper, plastic film of various transparencies and colors, resin balls, carbon fiber balls, or other material deleterious to the workpiece. These separate pieces of information are first used to classify (identify) the presence or absence of these features in the camera's 12 image frame, using both general mathematical techniques and specific and unique methods suggested by the nature of the workpiece being inspected, after which the importance of the particular set of features is weighted and/or selected to perform a further measurement of extent and type using other algorithms derived from empirical experience with the use of the system on a large range of actual workpieces. This last step of measurement may then be compared with engineered specifications for the particular portion of the workpiece to generate out-of-specification indicators for later correction or for use in conjunction with various methods of indicating flaw type and location to a human operator.

Figure 2:
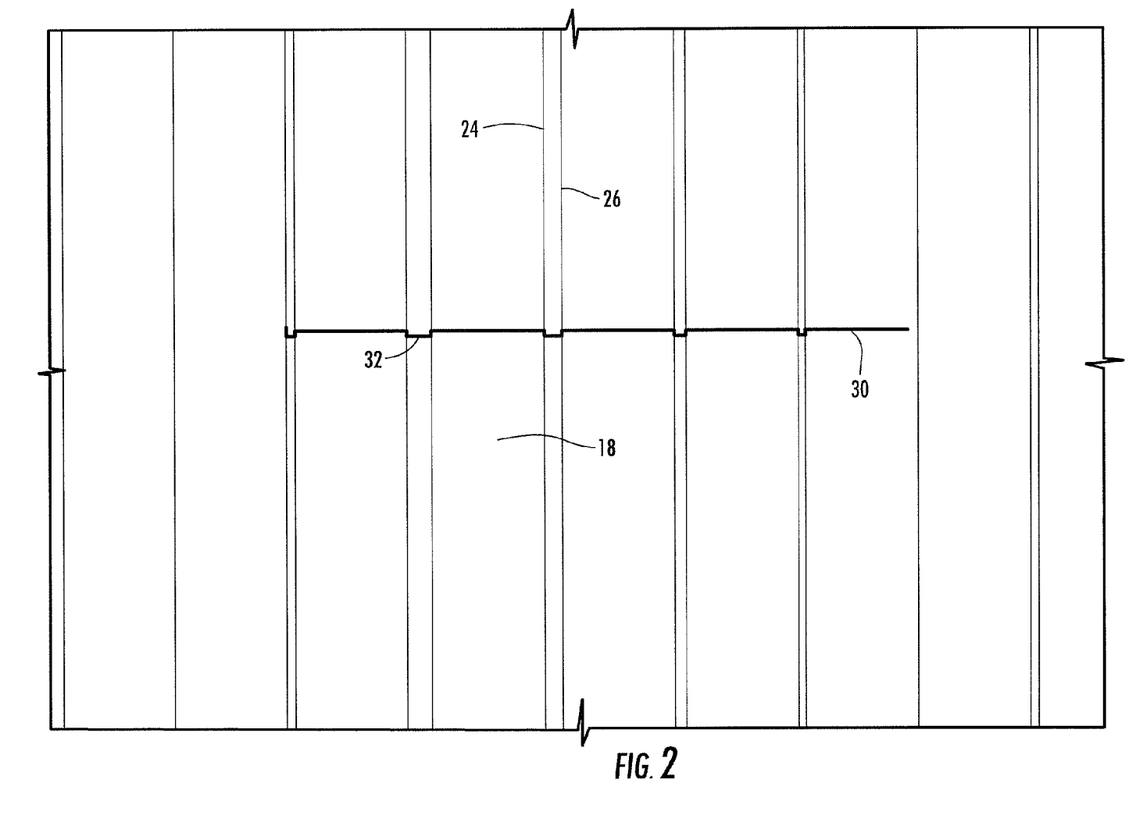
FIG. 2 is an image of a workpiece obtained using the inspection system of FIG. 1.

As shown in FIG. 2, an exemplary image of a workpiece 18 captured by a camera 12 is shown. The image demonstrates that the edges 24, 26 are clearly shown as continuous lines within the image frame, while the laser line 30 is also shown extending generally perpendicular to the lines indicative of the gap edges. Laser line 30, which depicts a narrow slice of the image, includes a plurality of "steps" (discontinuities, jogs, or gap indications) 32 that also correspond to the edges 24, 26 of the gap 28. Thus, the combination of the three sets of data from each of the laser generator and LED arrays 14abc allows a more accurate depiction and analysis of the workpiece 18 in the presence of noise or other sources of distortion that could affect the reliability of the inspection process. In addition, the image would typically depict colored features indicative of the edges 24, 26 and gap 28 such that the three-dimensional information (wherein analysis in data system 16 is engaged with the surface topology) does not affect the two-dimensional information contained therebelow (i.e., portions of the image generally illuminated by the combination of the colored LED arrays 14*bc* and over which the analysis performed in data system 16 is only sensitive to surface reflectivity regardless of topology). Thus, the two-dimensional and three-dimensional information may be readily differentiated from one another. In other words, being that the laser generator(s) 14*a* are of a color differentiable from the LED arrays 14*bc*, all surface information in a given frame is available to two-dimensional analysis in data system 16, without interference from the three-dimensional analysis provided at the portions of the surface illuminated by the laser generator(s) 14*a*. However, it is understood that the LED arrays 14*bc* could be configured to illuminate the workpiece 18 such that an image provides three-dimensional information regarding a particular feature desired to be detected.

Figure 4:
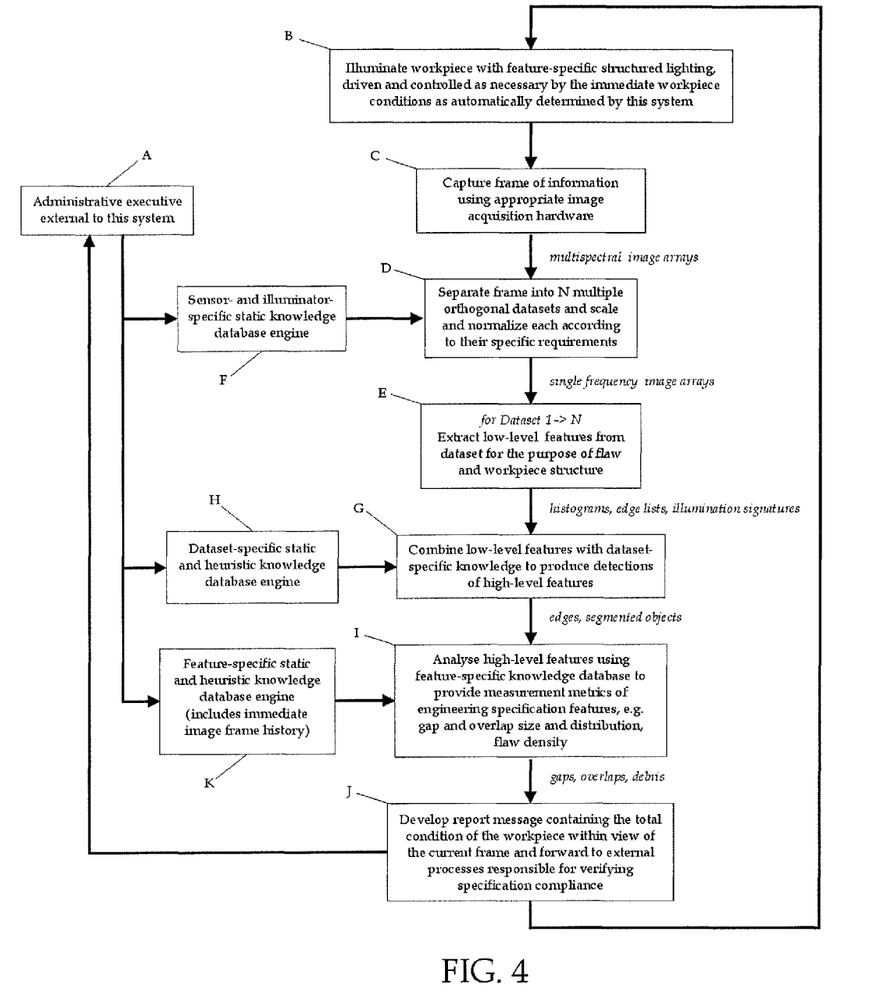
FIG. 4 is a flowchart illustrating a method for inspecting a workpiece according to one embodiment of the present invention.

FIG. 4 depicts a method for inspecting a workpiece according to one embodiment of the present invention. The method generally includes illuminating at least a portion of the workpiece 18 with a plurality of colored structured illumination generated by a respective laser generator 14*a* and LED arrays 14*bc* (block B). Moreover, the method includes utilizing a multispectral camera 12 to capture one or more multicomponent images of the workpiece 18 including the structured illumination incident thereon (block C). The component images are then separated and individually normalized in a nominal fashion (block D) using a knowledge database (block F), resulting in datasets specific to each camera color band. The knowledge database generally includes expected properties of various features that are based on the characteristics of the illuminated workpiece. Low-level features, e.g., histograms, are calculated and collected (block E) for each of these datasets and forwarded to a higher-level process (block G), which uses a knowledge database (block H) to derive more advanced features, e.g. line edges and contiguous objects. The database process (block H) for these operations may dynamically change over time based on information gained during the operation of the system, and thus is typically a heuristic system. These high-level features are then passed to the top-level recognition process (block I) that determines the presence or absence of the desired workpiece features, e.g., gaps or overlaps between adjacent composite tape courses, and the presence or absence of undesired workpiece features, e.g. debris, wrinkles, puckers, etc. The recognition process is aided by another database (block K) similar to that described above (block H) except that it is designed to support the recognition level, and to optionally use one or more of the immediately previous frame(s) for additional information. For example, in this embodiment of the present invention, the recognition process (block I) might build up confidence in the detection of a tape wrinkle based upon a combination of two-dimensional information from a given image frame and three-dimensional information from several preceding frames. The final step of this entire process is to prepare high-level output (block J), including both desired and undesired attributes of the current workpiece state, for transmission to an external administrative process (block A), which is responsible for any preservation of data and/or initiation of any real-time methods of display for human operators.

Because the information from each of the color channels corresponding to a respective illumination sources 14*abc* is orthogonal (i.e., each is independent from one another), the data system 16 employs algorithms to detect and measure the presence of a feature indicative of the workpiece 18 using a simultaneous combination of all three data sets. The algorithms analyze laser line signatures generated by the laser generators 14*a* that may be unfocused or "fuzzy." The algorithms may provide for individual laser signature isolation by color separation, signature tracking during motion of the workpiece by analyzing an anisotropic histogram of the overall image frame, and the extraction of small discontinuous features from noisy image power by standard image segmentation and "blob" processing. In these algorithms, the data system 10 uses knowledge of each laser fan beam's or LED light wash's color, shape, and source location and direction. The data system 16 thus may provide two-dimensional (any information other than that resulting from illumination of the workpiece by means of laser fan beams) and three-dimensional (that associated with the illumination of the workpiece by means of laser fan beams) measurement of any features associated with the workpiece 18 such that these features may be identified in order to, for example, repair the workpiece, facilitate further processing of the workpiece, or provide a location for projection of flaw type and location onto the workpiece. Thus, two-dimensional information may relate to the information captured by a camera from the perspective of a plan view, while three-dimensional information (e.g., depth) may relate to information captured by the camera associated with the illumination beams illuminated on the workpiece at a desired incidence angle. For instance, the data system 16 could provide the width and height of a gap in a workpiece 18, as well as the specific location of a feature of the workpiece. According to one embodiment, encoders could be employed to provide positional information for locating features identified during the inspection process. For example, a composite tape lamination machine could utilize encoders on tape laying heads and/or the gantry to provide positional information that could be correlated with the images obtained by the camera 12. In addition, or alternatively, the system can utilize a common time base (precision clock) to tag all outputs such that the location of detected features can be derived by correlating with time-tagged machine head and/or gantry locations recorded by a separate machine control system.

Thus, embodiments of the present invention may provide several advantages. For example, the data system 16 is capable of analyzing images to provide both two-dimensional and three-dimensional information indicative of a workpiece 18. The use of a plurality of laser generators and LED arrays 14*abc* increases the depth of field for moving workpieces 18, increases the surface sampling density so that small features are not overlooked during inspection, and enables the deployment of the same laser generators for large, static inspections. In addition, the system 10 utilizes fan beams having a shallow incidence angle that is configured to detect specific features of a workpiece to improve the accuracy of identifying the same, as well as identifying surface debris in order to differentiate actual features from common structures associated with the workpiece (e.g., ridge-like structures in the central regions of composite tape material). Moreover, the system 10 is capable of inspecting the workpiece 18 during processing and in real time, which may reduce down time and increase efficiency. The system 10 employs a color camera 12 in order to separate two-dimensional from three-dimensional laser signatures using spectral components to increase the two-dimensional surface coverage and to increase the rate of inspection by the simple mechanism of orthogonal color separation into independent but simultaneously acquired image frames that are analyzed separately from one another. Thus, the system 10 provides a hybrid of two-dimensional and three-dimensional information that enables inspection of workpieces 18 having various surface configurations in a single image frame interval.

Many modifications and other embodiments of the invention set forth herein will come to mind to one skilled in the art That which is claimed:

1. An inspection system for inspecting a moving workpiece, the system comprising:
   a plurality of illumination sources positioned proximate to the workpiece and each operable to illuminate at least a portion of the workpiece with at least one respective illumination beam, each illumination beam having a different respective color;
   at least one camera positioned proximate to the workpiece and operable to capture at least one image of at least a portion of the workpiece illuminated by the illumination beams; and
   a data system capable of providing information indicative of the workpiece based on the image acquired by the camera;
   wherein the plurality of illumination sources includes at least one LED array;
   wherein the plurality of illumination sources further comprises at least one laser fan beam generator;
   wherein the at least one laser fan beam generator is arranged to generate a laser beam at an oblique incidence angle, and thereby produce a line of laser light on the workpiece, the line being generally perpendicular to a direction of motion of the workpiece, and
   the at least one LED array is arranged to generate a light wash on the surface of the moving workpiece; and
   wherein the said information is two-dimensional and three-dimensional information, the two-dimensional information resulting from the illumination of the workpiece by the light wash, and the three-dimensional information resulting from the illumination of the workpiece by the laser fan beam.

2. The system according to claim 1, wherein the plurality of illumination sources produce respective illumination beams that are configured to illuminate a respective feature of the workpiece.

3. The system according to claim 1, wherein the incidence angle of the laser beam generated by the at least one laser fan beam generator is measured between a line drawn parallel to the workpiece and the laser beam.

4. The system according to claim 3, wherein the incidence angle is less than 30°.

5. The system according to claim 1, wherein the data system is capable of providing at least one of information indicative of respective edges of the workpiece, a gap in the workpiece, a topology of the workpiece, a shape of the workpiece, and a potential flaw in the workpiece.

6. The system according to claim 1, wherein the data system is capable of providing the said information during processing of the workpiece.

7. A method for inspecting a moving workpiece, the method comprising:
   illuminating at least a portion of the workpiece with a plurality of colored illumination beams;
   capturing at least one image of at least a portion of the workpiece illuminated by the illumination beams; and
   providing information indicative of the workpiece based on the captured image;
   wherein the said illuminating includes generating illumination using at least one LED array;
   wherein said illuminating further comprises generating illumination using at least one laser fan beam generator;
   wherein the at least one laser fan beam generator generates a laser beam at an oblique incidence angle, and thereby produces a line of laser light on the workpiece, the line being generally perpendicular to a direction of motion of the workpiece, and
   the at least one LED array generates a light wash on the surface of the moving workpiece; and
   wherein the said information is two-dimensional and three-dimensional information, the two-dimensional information resulting from the illumination of the workpiece by the light wash, and the three-dimensional information resulting from the illumination of the workpiece by the laser fan beam.

8. The method according to claim 7, further comprising performing a manufacturing process on the moving workpiece during the illuminating and capturing steps.

9. The method according to claim 7, wherein the incidence angle of the laser beam generated by the at least one laser fan beam generator is being measured between a line drawn parallel to the workpiece and the laser beam.

10. The method according to claim 9, wherein the incidence angle is less than 30°.

11. The method according to claim 7, wherein the said providing comprises providing at least one of information indicative of respective edges of the workpiece, a gap in the workpiece, a topology of the workpiece, a shape of the workpiece, and a potential flaw in the workpiece.

* * * * *